United States Patent [19]

Biedermann

[11] Patent Number: 5,490,822
[45] Date of Patent: Feb. 13, 1996

[54] ORTHESIS JOINT

[75] Inventor: Lutz Biedermann, Schwenningen, Germany

[73] Assignee: Biedermann Motech GmbH, Schwenningen, Germany

[21] Appl. No.: 293,123

[22] Filed: Aug. 19, 1994

Related U.S. Application Data

[63] Continuation of Ser. No. 973,073, Nov. 6, 1992, abandoned.

[30] Foreign Application Priority Data

Nov. 11, 1991 [DE] Germany .................. 41 37 056.2

[51] Int. Cl.⁶ ........................................... A61F 5/00
[52] U.S. Cl. ............................... 602/16; 602/26
[58] Field of Search ...................... 602/5, 16, 26

[56] References Cited

U.S. PATENT DOCUMENTS

| | | | |
|---|---|---|---|
| 4,372,298 | 2/1983 | Lerman | 602/26 |
| 4,493,316 | 1/1985 | Reed et al. | 602/26 X |
| 4,697,583 | 10/1987 | Moson et al. | |
| 4,791,916 | 12/1988 | Paez | 602/26 |
| 4,803,975 | 2/1989 | Meyers | 602/26 |
| 4,928,670 | 5/1990 | DeLorenzo | 602/26 |
| 5,005,565 | 4/1991 | Fratesi | 602/16 |
| 5,042,464 | 8/1991 | Skwor et al. | 602/16 |

*Primary Examiner*—Linda C. Dvorak
*Attorney, Agent, or Firm*—Donald Brown

[57] ABSTRACT

An orthesis joint is provided which has a first support plate, a thigh attachment part hingedly connected thereto through a first bearing bush, a lower leg attachment part connected with the first support plate through a second bearing bush and a connecting member hingedly connected with both attachment parts through a third and fourth bearing bush. Such an orthesis joint is in particular used for knee ortheses. In order to prevent the orthesis joint from chafing at the knee when flexing or stretching the joint a pressure cushion is provided which is carried by the connecting member.

12 Claims, 2 Drawing Sheets

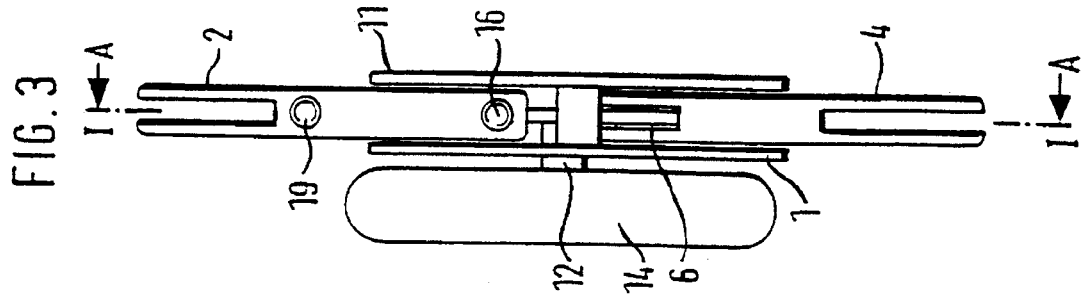
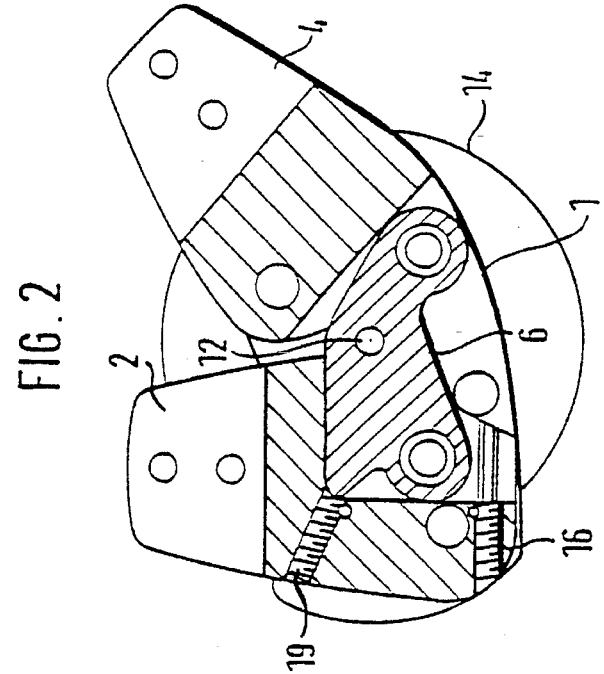
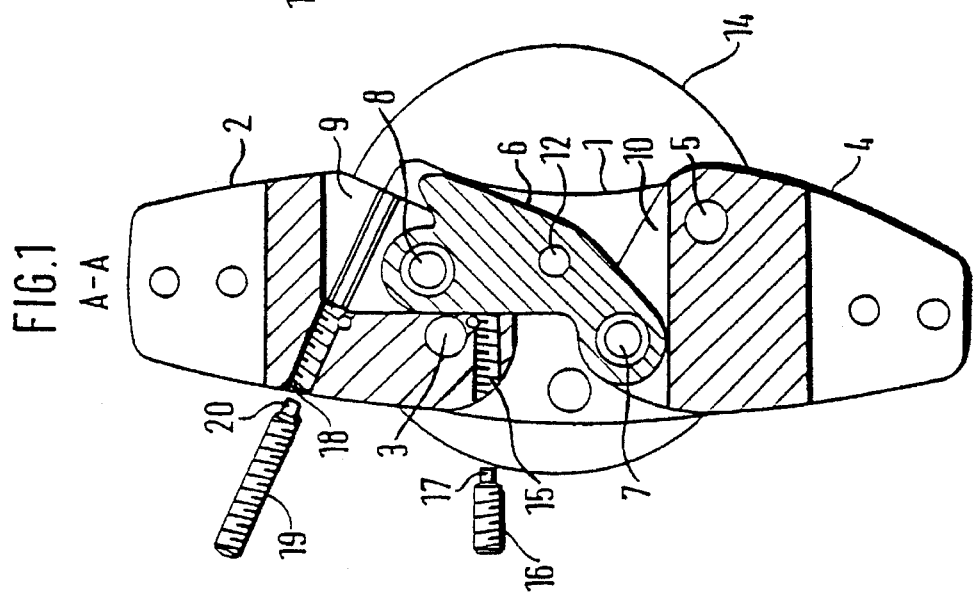

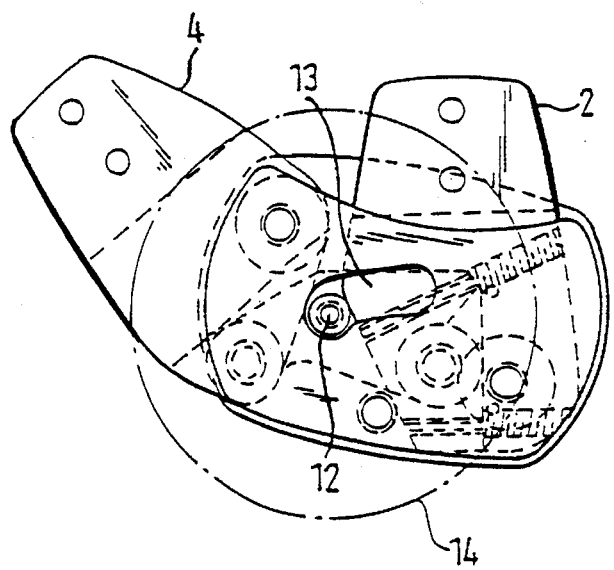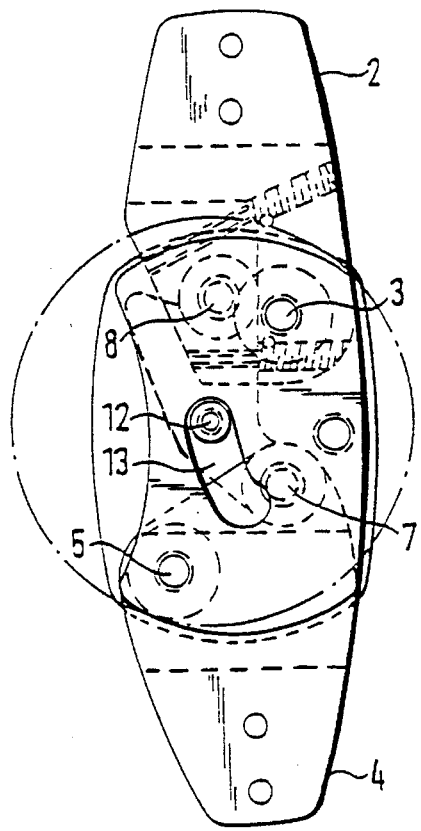

ORTHESIS JOINT

This is a continuation of application(s) Ser. No. 07/973,073 filed on Nov. 6, 1992, now abandoned.

BACKGROUND OF THE INVENTION

The invention relates to an orthesis joint and in particular to an orthesis joint for a knee or leg orthesis.

Such an orthesis joint is disclosed in the U.S. Pat. No. 4,886,054. The orthesis joint is in particular used as a knee joint for leg or theses. For preventing chafing of the support plate at the knee a prior used orthesis which is constructed according to the teaching of the U.S. Patent comprises a pressure cushion which is arranged at the side of the support plate facing the knee and which is rigidly connected to the support plate. This pressure cushion has the disadvantage that every flexion and stretching causes a change of position thereof because of the path of movement resulting from the two joints. In other words, the pressure cushion constantly moves up and down or back and forth, respectively, at the knee.

OBJECTS OF THE INVENTION

It is an object of the invention to provide an improved orthesis joint in which the above-mentioned drawbacks are avoided. It is a further object of the invention to provide an orthesis joint which avoids an up-and-down or back-and-forth movement of the cushion member when flexing or stretching the orthesis joint. It is a still further object of the invention to provide an orthesis joint which prevents the chafing of the cushion member in use of the orthesis.

SUMMARY OF THE INVENTION

In order to achieve the above-mentioned objects the invention provides an orthesis joint comprising a first support plate, a thigh attachment part which is hingedly connected to said first support plate through a first bearing bush, a lower leg attachment part which is hingedly connected to said first support plate through a second bearing bush, a connecting member which is hingedly connected to both said attachment parts through a third and fourth bearing bush, respectively, a pressure cushion and means supporting said pressure cushion on said connecting member.

BRIEF DESCRIPTION OF THE DRAWINGS

Further features and advantages of the invention result from the description of an embodiment with reference to the Figures. In the Figures:

FIG. 1 is a sectional view along line A—A in FIG. 3 with the orthesis joint being in stretched end position;

FIG. 2 is a corresponding representation of the joint in flexed end position;

FIG. 3 is a front view of the orthesis joint;

FIG. 4 is a back view of the orthesis joint shown in FIG. 2 with pressure cushion indicated in lines; and FIG. 5 is a back view of the orthesis joint shown in FIG. 1 with the pressure cushion indicated in lines.

DESCRIPTION OF A PREFERRED EMBODIMENT

The orthesis joint comprises a first support plate (1). A thigh attachment part (2) is hingedly connected thereto at a bearing bush (3) extending perpendicular to the plane of the support plate. Further, a lower leg attachment part (4) is provided which is hingedly connected with the support plate (1) at a second bearing bush (5) extending perpendicular to the plane of the support plate. A connecting member (6) is provided between both attachment parts. This connecting member has one end thereof hingedly connected to the lower leg attachment part (4) at a third bearing bush (7) and the other end thereof hingedly connected to the thigh attachment part (2) at a fourth bearing bush (8).

The connection between the connecting member and the attachment parts is made such that slotted recesses (9, 10) extending parallel to the support plate are provided at the facing ends of the attachment parts. The connecting member is movably guided within these recesses. As may be best seen from FIG. 3, a second sup port plate (11) is provided which is a mirror image of the first support plate. The ends of the respective bearing bushes which are facing away from the first support plate are supported in the second support plate. The attachment parts are freely movable between both support plates.

The position of the first to fourth bearing bushes is selected in per se known manner such that a first straight line connecting the first and second bearing bush intersects the second straight line connecting the third and fourth bearing bushes with an angle such that a motion having a substantially circular portion and a following substantially spiral portion results from the two joints formed by the first and second bearing bushes when moving the attachment parts or the orthesis connected thereto, respectively. The connecting member (6) has a threaded bush (12). In FIGS. 1 and 2 the rear side of the rivet connecting the threaded bush with the connecting member can be seen, whereas the threaded bush itself is shown in FIGS. 3 to 5. The first support plate (1) comprises a hole (13) having a size such that the threaded bush (12) can freely move through the hole when moving the orthesis joint. A pressure cushion (14) is rigidly connected to the connecting member (6) through the threaded bush (12) by means of a suitable screw. As may be best seen in FIG. 1, the threaded bush (12) is arranged on a line which extends perpendicular to the longitudinal axis of the stretched orthesis joint and which is about equally spaced from the first bearing bush (3) and from the second bearing bush (5). In a side view it is positioned on a straight line which extends parallel to the longitudinal axis of the stretched orthesis joint and which is about equally spaced from the first and second bearing bush. The rigid connection of the pressure cushion with the connecting member (6) achieves that the pressure cushion no longer moves up and down or back and forth, respectively, when moving the orthesis joint.

As may be best seen in the FIGS. 1 and 2, a first threaded bore (15) is provided in the center plane of the thigh attachment part (2) and extends parallel to the support plate. A threaded sleeve (16) comprising a stop (17) which is prestressed by an interior spring is screwed into the bore (15). The screw is adjusted, dependent on the needs of the patient, such that the stretched end position shown in FIG. 1 is defined by the stop. Further, a second threaded bore (18) is provided and a corresponding threaded sleeve (19) having a stop (20) prestressed by an interior spring screwed into the threaded bore (18). As may in particular be seen from FIG. 2, the flexed end position of the orthesis joint is defined by the screw-in location of the threaded sleeve with the stop. The spring's prestress or an elastic prestress produced by means of a rubber, if desired, respectively, prevents a hard collision of the orthesis parts when wearing the same, so that the wearing comfort is considerably improved.

Although the invention has been described with reference to specific example embodiment, it is to be understood that it is intended to cover all modifications and equivalents within the scope of the appended claims.

What is claimed is:

1. An orthesis joint comprising a first plate, a second plate, a thigh attachment part and a leg attachment part, a first bushing coupling said thigh attachment part to said first and second plates, a second bushing coupling said leg attachment part to said first and second plates, said leg and thigh attachment parts having slotted recesses in which a connecting member is positioned, said connecting member coupled to said leg attachment part and said thigh attachment part, said second plate having a portion defining a hole, a bush coupled to said connecting member and which also extends through said hole, said attachment parts and connecting member coupled together for relative rotatable movement with respect to each other and said plates and a pressure cushion member coupled to said bush on the side of said hole opposite said hole side closest to the connecting member so that the pressure cushion will not interfere with the movement of the attachment parts and move with the connecting member as the thigh part and leg part are rotatably moved relative to one another.

2. The joint of claim 1 in which said connecting member has a stop portion which engages a spring loaded member positioned in one of the attachment members and extending into said slotted recess thereof when the attachment parts are rotated towards each other.

3. The joint of claim 1 in which a spring loaded member is supported by one of said attachments for limiting the movement of said attachment members when the attachment members are rotated away from each other.

4. An orthesis joint comprising a first support plate,
   a thigh attachment part which is hingedly connected to first support plate through a first bearing bush,
   a lower leg attachment part which is hingedly connected to said first support plate through a second bearing bush,
   a connecting member which is hingedly connected to both said attachment parts through a third and fourth, respectively, bearing bush,
   a pressure cushion for preventing the orthesis joint from chafing at the knee when stretching or flexing the joint
   a connector supporting and coupled to said pressure cushion and said connecting member to rigidly connect said pressure cushion to said connecting member for movement therewith.

5. The joint of claim 4 in which said first support plate defines a hole into which said connector extends and in which said connector comprises a bearing bush to which the cushion is rigidly connected.

6. The orthesis joint of claim 4, wherein said pressure cushion has a center which is positioned essentially on a line extending perpendicular to the longitudinal direction of said orthesis joint when stretched and which is about equally spaced from said first and second bearing bushes.

7. The orthesis joint of claim 5, comprising a slotted recess provided in one of said attachment parts at the portion thereof facing the other of said attachment parts, said connecting member being guided within said slotted recess.

8. The orthesis joint of claim 5, comprising a second support plate disposed at a side opposite to said first support plate, a hole in one of said support plates and a joining element connecting said connection member and said pressure cushion, said joining element extending through said hole.

9. The orthesis joint of claim 5, comprising a first stop and a second stop for defining the relative movement of said attachment parts and said connecting member, at least one of said stops being adjustable.

10. The orthesis joint of claim 9, wherein at least one of said stops is elastic.

11. The orthesis joint of claim 9, wherein said stops are designed as threaded sleeves, said threaded sleeves being supported in a threaded bore and having spring-biased stop heads.

12. The orthesis joint according to claim 9, wherein said stops are provided in one of said attachment parts and extend into said slotted recess.

* * * * *